(12) United States Patent
Bonrath et al.

(10) Patent No.: US 9,371,279 B2
(45) Date of Patent: Jun. 21, 2016

(54) TRANSESTERIFICATION PROCESS OF RETINOL ESTERS

(71) Applicant: DSM IP ASSETS B.V., Heerlen (NL)

(72) Inventors: Werner Bonrath, Basel (CH); Alex Gaa, Basel (CH); Claude Stritt, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/419,848

(22) PCT Filed: Aug. 7, 2013

(86) PCT No.: PCT/EP2013/066558
§ 371 (c)(1),
(2) Date: Feb. 5, 2015

(87) PCT Pub. No.: WO2014/023772
PCT Pub. Date: Feb. 13, 2014

(65) Prior Publication Data
US 2015/0183734 A1  Jul. 2, 2015

(30) Foreign Application Priority Data

Aug. 7, 2012 (EP) .................................. 12179461

(51) Int. Cl.
*C07C 403/12* (2006.01)

(52) U.S. Cl.
CPC ........... *C07C 403/12* (2013.01); *C07C 2101/16* (2013.01)

(58) Field of Classification Search
CPC ...................................................... C07C 67/02
See application file for complete search history.

(56) References Cited

U.S. PATENT DOCUMENTS 2,971,966 A * 2/1961 Stieg et al. .................... 554/163
2008/0085534 A1   4/2008 Boaz et al.

FOREIGN PATENT DOCUMENTS

WO   WO 2004/044212   5/2004

OTHER PUBLICATIONS

International Search Report for PCT/EP2013/066558, mailed Oct. 28, 2013, 2 pages.
Soukup et al., "Preparation of (7Z)- and (7Z,11Z)—Vitamin A", Tetrahedron Letters, vol. 32, No. 33, pp. 4117-4118, (Aug. 12, 1991), 2 pages.

* cited by examiner

*Primary Examiner* — Brian J Davis
(74) *Attorney, Agent, or Firm* — Nixon & Vanderhye P.C.

(57) ABSTRACT

The present invention relates to a transesterification process of specific compounds comprising isoprenoid units.

8 Claims, No Drawings

TRANSESTERIFICATION PROCESS OF RETINOL ESTERS

This application is the U.S. national phase of International Application No. PCT/EP2013/066558, filed 7 Aug. 2013, which designated the U.S. and claims priority to EP Application No. 12179461.4, filed 7 Aug. 2012, the entire contents of each of which are hereby incorporated by reference.

The present invention relates to a transesterification process of specific compounds comprising isoprenoid units.

Transesterification processes of compounds comprising isoprenoid units are usually carried out by using chloride acids, such as described by Soukup et al. in Tetrahedron Letters Vol. 32 (33), p. 4117-4118, 1991.

In view of the ecological problems of halogenides (waste issues), it is desirable to avoid such compounds.

But nevertheless an alternative process should be comparable to the processes of the prior art in regard to
(i) energy consumption, and
(ii) yields, and
(iii) reaction time.

Therefore the goal of the present invention was to find a new transesterification process without the disadvantages of the processes of the prior art as listed above.

Surprisingly, a new process for transesterification of compounds of formula (I)

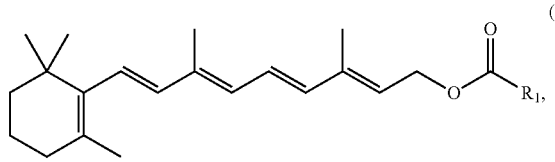

wherein $R_1$ is —$CH_3$ or —$CH_2CH_3$,
has been found, which is carried out with a specific catalyst.

The newly found transesterification process is characterised in that it is a one step process, an easy to handle process with excellent yields of the end product.

The transesterification process is carried under very mild reaction conditions (low energy consumption!).

The side products can be removed easily (for example by distillation). This can be done after the reaction is finished as well as during the reaction takes place (continuously).

The catalyst which is used is at least one alkali hydroxide and/or at least one earth alkali hydroxide solved in alcohol (or a mixture of alcohols).

Preferably the alkali hydroxide and/or the earth alkali hydroxide is $Ca(OH)_2$, CsOH, KOH and/or NaOH.

The amount of the catalyst used in the transesterification process according to the present invention is about 0.1%-1.5% of the total amount of the compound of formula (I), preferably 0.2%-1%.

The alcohol (or the mixture of alcohols) should preferably be liquid at a temperature of around 30° C. Usually (and preferably) methanol, ethanol isopropanol and/or tert-butanol is used.

The ratio of alkali hydroxide to alcohol goes from 1:2 to 1:10, preferably from 1:3 to 1:6.

The alkali hydroxide and/or the earth alkali hydroxide (or a mixture of such hydroxides) and the alcohol (or a mixture of alcohols) are usually added to the reaction as a mixture (alkali hydroxide(s) solved in alcohol(s). But it is also possible to add the two compounds (alkali hydroxide (or a mixture of alkali hydroxides) and the alcohol (or a mixture of alcohols)) separately.

Therefore the present invention relates to a transesterification process of a compound of formula (I)

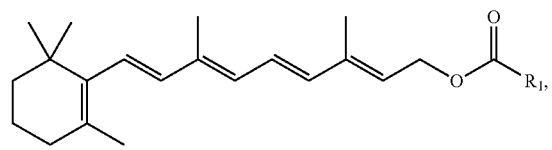

with $R_1$ defined as —$CH_3$ or —$CH_2CH_3$,
wherein the compound of formula (I) is reacted with at least one compound of formula (II)

wherein
$R_2$ signifies a $C_3$-$C_{15}$ alkyl moiety or a $C_2$-$C_{18}$ alkenyl moiety, in the presence of at least one alkali hydroxide and/or at least one earth alkali hydroxide which is solved in at least one alcohol.

It also possible that a mixture of compounds of formula (I) wherein $R_1$ is —$CH_3$ and wherein $R_1$ is —$CH_2CH_3$ is used for the process.

Compounds of formula (III)

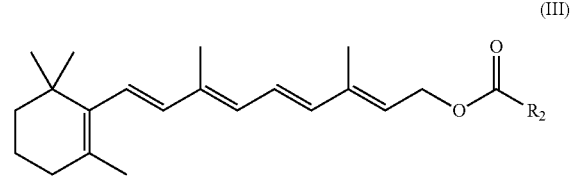

wherein $R_2$ has the identical meanings as in the corresponding compounds of formula (II),
are the reactions products of this process.

The side products which are removed from the reaction mixture are (mainly) compounds of formula (IV)

wherein $R_1$ has the same meanings as defined in compounds of formula (I).

It is clear that the $R_1$'s in one transesterification reaction are always identical for compounds of formula (I) and (IV).

It is also clear that the $R_2$'s in one transesterification reaction are always identical for compounds of formula (II) and (III).

The side products (compounds of formula (IV)) are low boiling compounds and therefore can be removed easily from the reaction mixture (for example by distillation).

When $R_2$ is a $C_3$-$C_{15}$ alkyl moiety, then preferably the alkyl moiety is linear. Preferred are —$C_{11}H_{23}$ (lauryl), —$C_{13}H_{27}$ (myristyl) and —$C_{15}H_{29}$ (palmityl).
Especially preferred is palmityl.

When $R_2$ is a $C_2$-$C_{18}$ alkenyl moiety, there are one or more C—C double bonds and preferably the alkenyl moiety is linear.

It is also possible that a mixture of compounds of formula (II) is used for a transesterification, which then results in a mixture of the desired end-products.

A preferred embodiment of the present invention relates to a transesterification process of a compound of formula (I)

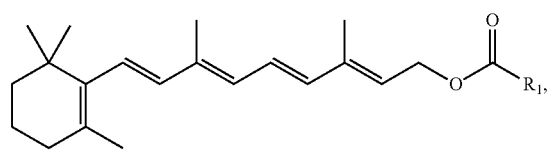
(I)

with $R_1$ defined as —$CH_3$ or —$CH_2CH_3$,
wherein the compound of formula (I) is reacted with a compound of formula (II)

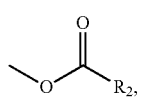
(II)

wherein
$R_2$ signifies a $C_3$-$C_{15}$ alkyl moiety or a $C_2$-$C_{18}$ alkenyl moiety, in the presence of Ca(OH)$_2$, CsOH, KOH and/or NaOH solved in at least one alcohol, which is chosen from the group consisting of methanol, ethanol, isopropanol and tert-butanol.

A further preferred embodiment of the present invention relates to a transesterification process of a compound of formula (I)

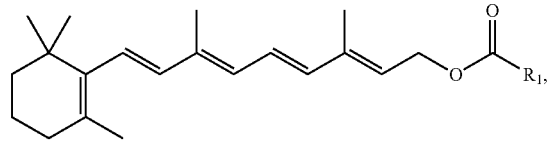
(I)

with $R_1$ defined as —$CH_3$ or —$CH_2CH_3$,
wherein the compound of formula (I) is reacted with a compound of formula (II)

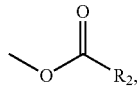
(II)

wherein
$R_2$ signifies a $C_3$-$C_{15}$ alkyl moiety or a $C_2$-$C_{18}$ alkenyl moiety, in the presence of Ca(OH)$_2$, CsOH, KOH and/or NaOH solved in at least one alcohol, which is chosen from the group consisting of methanol, ethanol, isopropanol and tert-butanol, and wherein the amount of the catalyst used in the transesterification is 0.1%-1.5% of the total amount of the compound of formula (I).

A more preferred embodiment of the present invention relates to a transesterification process of a compound of formula (I)

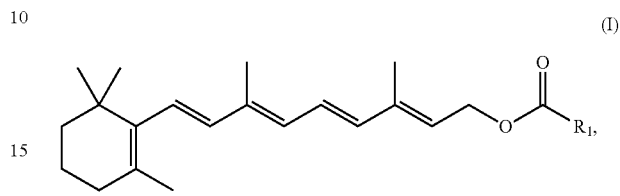
(I)

with $R_1$ defined as —$CH_3$ or —$CH_2CH_3$,
wherein the compound of formula (I) is reacted with at least compound of formula (II)

(II)

wherein
$R_2$ is —$C_{11}H_{23}$, —$C_{13}H_{27}$ and/or —$C_{15}H_{29}$, (preferably —$C_{15}H_{29}$),
in the presence of KOH and/or NaOH solved in at least one alcohol, which is chosen from the group consisting of methanol, ethanol, isopropanol and tert-butanol and wherein the ratio of KOH and/or NaOH to methanol, ethanol, isopropanol and/or tert-butanol goes from 1:2 to 1:10, preferably from 1:3 to 1:6.

A further more preferred embodiment of the present invention relates to a transesterification process of a compound of formula (I)

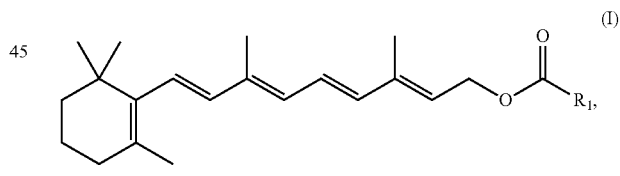
(I)

with $R_1$ defined as —$CH_3$ or —$CH_2CH_3$,
wherein the compound of formula (I) is reacted with at least compound of formula (II)

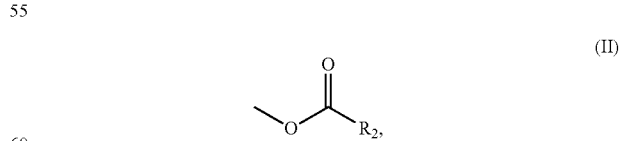
(II)

wherein
$R_2$ is —$C_{11}H_{23}$, —$C_{13}H_{27}$ and/or —$C_{15}H_{29}$, (preferably —$C_{15}H_{29}$),
in the presence of KOH and/or NaOH solved in at least one alcohol, which is chosen from the group consisting of methanol, ethanol, isopropanol and tert-butanol and wherein the ratio of KOH and/or NaOH to methanol, ethanol, isopropanol and/or tert-butanol goes from 1:2 to 1:10, preferably from 1:3 to 1:6, and wherein the amount of the catalyst used in the transesterification is 0.1%-1.5% (preferably 0.2%-1%) of the total amount of the compound of formula (I).

As stated above the reaction conditions of the new transesterification process are mild ones.

Usually the reaction is carried out at a slightly elevated temperature. Preferably the reaction temperature is between 20° C. and 80° C., more preferably between 30° C. and 70° C., even more preferred between 40° C. and 70° C.

Usually the reaction is carried out at reduced pressure (less than 101325 Pa). Preferably the pressure goes from 100 to 15000 Pa, more preferably 100-5000 Pa.

Usually the transesterification reaction is carried out in a solvent (or a mixture of solvents).

Suitable solvents are aliphatic $C_5$-$C_{15}$ hydrocarbons, which can be linear, branched or cyclic. Preferred are aliphatic $C_6$-$C_{12}$ hydrocarbons, which can be linear, branched or cyclic. More preferred are hexane, heptane, cyclohexane and methylcyclohexane.

Also suitable are aromatic solvents, such as toluene and xylene.

The starting material (compound of formula (I) and compound of formula (II)) are added at the start of the reaction in an equimolar ratio. Preferably compound of formula (II) is added in a slight excess.

Due to the fact that the reaction is usually carried out under reduced pressure, the reaction is usually terminated by bringing the reaction system to normal pressure. This should be done under inert conditions (in regard to the obtained product so that no further reaction, like i.e. oxidation takes place). Usually an inert gas or $CO_2$/water mixture is used for that purpose.

The compounds of formula (III) are obtained in excellent yields as well as in an excellent purity due to the fact that the side products are removed easily after or even during the reaction.

The following examples serve to illustrate the invention. All percentages are given in relation to weight and the temperature is given in degree Celsius.

EXAMPLES

Example 1

To 3000 kg of the compound of formula (Ia)

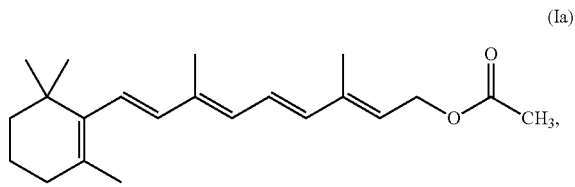 [SMILES: CC(=O)OC/C=C(C)/C=C/C=C(C)/C=C/C1=C(C)CCCC1(C)C]

which is known as Vitamin A acetate, in its crystalline form, 2750 kg of compound of formula (IIa)

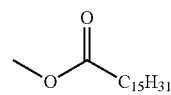

which is known as methyl palmitate have been added.

Afterwards 10 kg of NaOH have been dissolved in about 60 l of methanol, which was then added to the mixture of Vitamin A acetate and methyl palmitate.

This reaction mixture was heated up to 55° C. and the pressure was reduced to about 1500-2200 Pa. The reaction time was about 3 hours. During this process the main side product (methyl acetate) was removed continuously by distillation.

The reaction was stopped by the addition of water and $CO_2$.

Afterwards the compound of formula (IIIa)

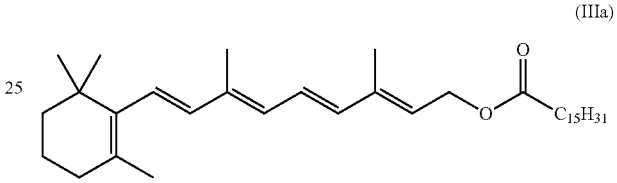

which is known as Vitamin A palmitate was isolated from the reaction solution by extraction.

The yield of compound of formula (IIIa) was 96%.

Example 2

To 110 g of the compound of formula (Ia)

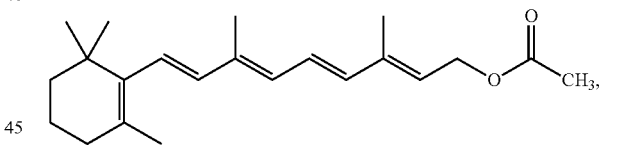

in its crystalline form,
a mixture consisting of 64.9 g of compound of formula (IIa)

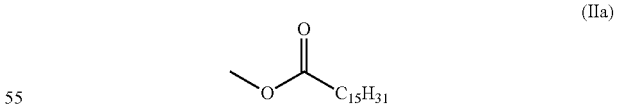

and
19.4 g of compound of formula (IIb)

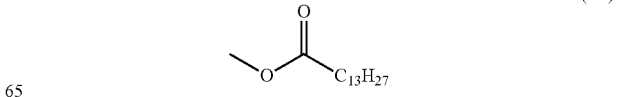

and 17.1 g of compound of formula (IIc)

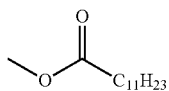
(IIc)

was added. This mixture was heated to 55° C. under $N_2$ atmosphere and a solution 0.88 g NaOH in 4.4 ml $CH_3OH$ was added at a pressure of 100-200 Pa. The reaction solution was stirred for about 4 hours at 55° C. at a pressure of 100-200 Pa.

Afterwards the reaction mixture was cooled and 416 ml of n-hexane and 270 ml of water was added and $CO_2$ was pumped though the solution.

The hexane phase was dried with potassium sulphate, filtered and the hexane was removed by distillation.

198 g of a mixture of the compounds (in a molar ratio of 3:1:1)

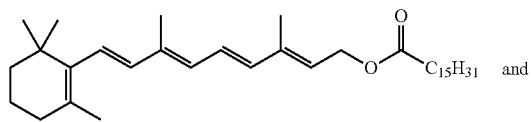
(IIIa) and

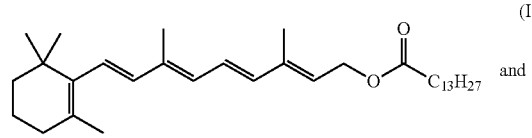
(IIIb) and

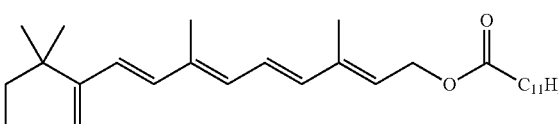
(IIIc)

was obtained.

Example 3a-3d

To 258 g of the compound of formula (Ia)

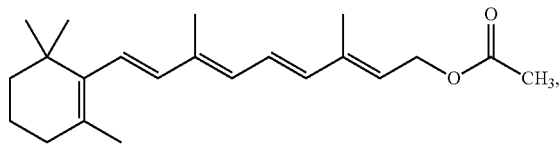
(Ia)

in its crystalline form, 219 g of compound of formula (IIa)

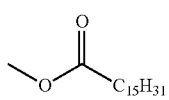
(IIa)

has been added. Afterwards this mixture was heated under $N_2$ to 55° C. and 21 g of a 10% $NaOH/CH_3OH$ solution was added.

This reaction mixture was heated up to 55° C. and the pressure was reduced to about 13000-660 Pa. The reaction time was about 3 hours. During this process the main side product (methyl acetate) was removed continuously by distillation.

The reaction was stopped by the addition $N_2$.

Afterwards the compound of formula (IIIa)

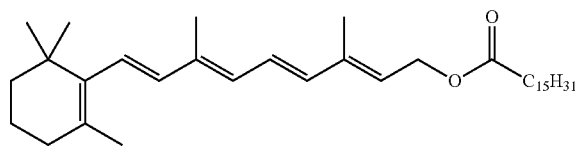
(IIIa)

was isolated from the reaction solution by extraction.

The yield of compound of formula (IIIa) was between 87.8 and 94.0%. The following table shows the yields in regard to the pressure.

| Example | Pressure [Pa] | Yield [%] |
| --- | --- | --- |
| 3a | 13000 | 87.8 |
| 3b | 6600 | 91.7 |
| 3c | 2600 | 93.3 |
| 3d | 1300 | 93.8 |
| 3e | 660 | 94.0 |

The invention claimed is:
1. A transesterification process for transesterification of a compound of formula (I):

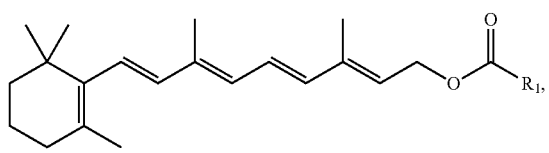
(I)

wherein $R_1$ is —$CH_3$,
the process comprises conducting a transesterification reaction under a reduced pressure of 100 to 15000 Pa and a temperature of between 20° C. and 80° C. by reacting the compound of formula (I) with a compound of formula (II):

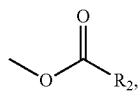
(II)

wherein
$R_2$ is a $C_3$-$C_{15}$ alkyl moiety or a $C_2$-$C_{18}$ alkenyl moiety,
in the presence of NaOH solved in at least one alcohol with a weight ratio of the NaOH to the at least one alcohol being from 1:2 to 1:10 to achieve a transesterification yield of 87.8% or greater.

2. The transesterification process according to claim 1, wherein $R_2$ is $C_{11}H_{23}$, $-C_{13}H_{27}$ and/or $-C_{15}H_{29}$.

3. The transesterification process according to claim 1, wherein the alcohol is at least one selected from the group consisting of methanol, ethanol, isopropanol and tert-butanol.

4. The transesterification process according to claim 1, wherein the alcohol is methanol.

5. The transesterification process according to claim 1, wherein the weight ratio of the NaOH to the at least one alcohol is from 1:3 to 1:6.

6. The transesterification process according to claim 1, wherein the transesterification process is carried out at a temperature between 30° C. and 70° C.

7. The transesterification process according to claim 1, wherein the reduced pressure is from 100 to 5000 Pa.

8. The transesterification process according to claim 1, which further comprises removing low boiling side products after or during the transesterification reaction.

\* \* \* \* \*